United States Patent [19]

Teng

[11] Patent Number: 5,599,950
[45] Date of Patent: Feb. 4, 1997

[54] PREPARATION PROCESS OF GINKGOLIDE B FROM GINKGOLIDE C

[75] Inventor: Beng-Poon Teng, Villeneuve Les Avignons, France

[73] Assignee: Societe de Conseils de Recherches et d'Applications Scientifiques (S.C.R.A.S), France

[21] Appl. No.: 287,632

[22] Filed: Aug. 4, 1994

[30]  Foreign Application Priority Data

Apr. 22, 1994 [GB]  United Kingdom ............... 9408044

[51] Int. Cl.$^6$ ............................................. C07D 307/93
[52] U.S. Cl. ............................................. 549/297
[58] Field of Search ............................................. 549/297

[56]  References Cited

U.S. PATENT DOCUMENTS

| | | | |
|---|---|---|---|
| 4,734,280 | 3/1988 | Braquet | 424/195.1 |
| 5,089,636 | 2/1992 | Kwak et al. | 549/297 |
| 5,241,084 | 8/1993 | Teng | 549/297 |

OTHER PUBLICATIONS

Morrison et al, "Organic Chemistry", 3rd edition, pp. 658–659, p. 527, 1981.
P. Braquet, Ginkgolides —Chemistry, Biology, Pharmacology and Clinical Perspectives,–1988–pp. XV, XVI, XVII.
Weinges K. et al. "Isolierung and Strukturaufklarung eines neuen Ginkgolids", Liebigs Ann Chem (1987), pp. 521–526.
Okabe et al. J. Chem. Soc. (c), 1967, vol. (21), pp. 2201–2206.
K. Weinges et al, "Herstellung von Ginkgolid B. aus Ginkgolid C", Liebigs Annalen Der Chemie, No. 1, Jan. 1991, pp. 81–83.

*Primary Examiner*—C. Warren Ivy
*Assistant Examiner*—Ba K. Trinh
*Attorney, Agent, or Firm*—Lucas & Just

[57]  ABSTRACT

A two-step process for converting ginkgolide C into ginkgolide B is disclosed. In the first step, ginkgolide C is reacted with a sulfonic anhydride to obtain a C-7 sulfonate of ginkgolide C. In the second step, the C-7 sulfonate of ginkgolide C is reacted with a borohydride, and this reaction eliminates the C-7 radical of the C-7 sulfonate of ginkgolide C, thus producing ginkgolide B.

12 Claims, No Drawings

PREPARATION PROCESS OF GINKGOLIDE B FROM GINKGOLIDE C

The present invention relates to ginkgolides and, in particular, to a process for converting ginkgolide C into ginkgolide B.

Ginkgolides are diterpene lactones which are isolated from the leaves and roots of the ginkgo biloba tree. Ginkgolides B and C are the predominant ginkgolides extracted, and they are extracted in approximately equal quantities. Ginkgolide B has been found to be a potent inhibitor of PAF-acether, see for example U.S. Pat. No. 4,734,280. Ginkgolide C has some activity, but at the present time is not nearly so desirable as ginkgolide B. The extraction of the ginkgolides is a costly process. As far as the applicant knows, there is no way to "selectively" extract only ginkgolide B; all of the ginkgolides are extracted and then are isolated from each other. Therefore, a process for converting ginkgolide C to ginkgolide B is of definite interest.

Ginkgolides B and C are quite similar chemically. The chemical formula of ginkgolide B is as follows:

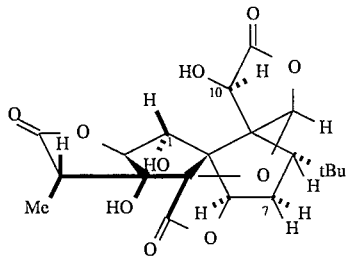

The chemical formula of ginkgolide C is as follows:

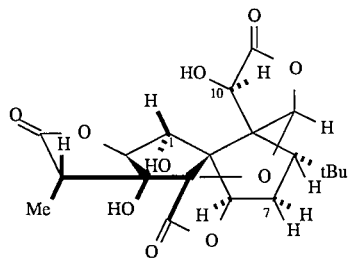

As can be seen, the only difference between the two is that one of the hydrogens at the 7-position of ginkgolide B is a hydroxyl group in ginkgolide C.

U.S. Pat. No. 5,241,084 discloses a process for converting ginkgolide C to ginkgolide B. The process is a rather lengthy four-step process and consists of the following four successive steps:

protecting the 10-hydroxy group of ginkgolide C by conversion to an alkyl ester, the reaction being effected in dimethylformamide at a temperature of from 15° to 50° C. for from 4 to 10 hours;

activating the 7-hydroxy group of the resultant 10-protected ginkgolide C by conversion to a (R) thiocarbonylester, the activation being effected in basic conditions at a temperature of from 0° to 40° C. for from 1 to 24 hours;

deoxygenating the 7-activated group in the resultant 10-protected 7-activated ginkolide C by treating it with tributyltin hydride or tris-(trimethylsilyl)silane, in an aprotic solvent, in the presence of a free-radical generator, the reaction being effected at a temperature of from 70° to 110° C. for from 15 minutes to 3 hours under inert atmosphere; and cleaving the protecting group from the 10-hydroxygroup of the resultant 10-protected ginkgolide B.

While the process of the '084 patent is very valuable in that the conversion of ginkgolide C to ginkgolide B by the four-step process is much less expensive than the extraction of ginkgolide B from the ginkgo tree, a simpler process would be even more valuable.

The applicant has now discovered a process for converting ginkgolide C to ginkgolide B in only two steps. The applicant's two-step process is as follows:

reacting ginkgolide C with a sulfonic anhydride to obtain a C-7 sulfonate of ginkgolide C, the reaction being effected in a basic medium at a temperature of from about −20° C. to about 35° C. and for a period of from about 15 minutes to about 3 hours; and reacting the C-7 sulfonate of ginkgolide C with a borohydride in an aprotic solvent, the reaction being effected at a temperature of from about 10° C. to about 30° C. and for a period of from about 15 minutes to about 3 hours, the reaction eliminating the C-7 radical of the C-7 sulfonate of ginkgolide C, thus producing ginkgolide B.

The first step of the two-step process is carried out in a basic medium. The solvent used is preferably pyridine, a mixture of pyridine and dichloromethane, a mixture of acetonitrile and triethylamine, 4-dimethylaminopyridine (DMAP) or imidazole. It is most preferred that the reaction be carried out in pyridine using from 1 to 4 equivalents of the trifluoromethane sulfonic anhydride.

The sulfonic anhydrides useful in the present invention are $R_1$-sulfonic anhydrides, i.e. $(R_1SO_2)_2O$, wherein $R_1$ is selected from the group consisting of a halogen, a lower alkyl ($C_1$–$C_6$), a halogen substituted lower alkyl, a phenyl, or a halo- or nitro-substituted phenyl. Preferred substituents for R are methyl, n-butyl, trifluoromethyl, toluene, p-nitrophenyl, p-bromophenyl and 2,4,6-trinitrophenyl.

The borohydrides useful in the second step of the present invention are $R_2$-borohydrides wherein $R_2$ is selected from the group consisting of metal or an alkyl, aryl or alkyl-aryl substituted ammonium.

The preferred alkali metal borohydride is sodium borohydride. Suitable ammonium borohydrides are tetraarylalkylammonium borohydride and tetraalkylammonium borohydride wherein alkyl group can have from 1 to 6 carbons and the aryl group may be a single or double ring. The preferred ammonium borohydride is tetrabutylammonium borohydride. The second step is preferably carried out in tetrahydrofuran (THF).

These and other aspects of the present invention may be more fully understood with reference to the following examples.

EXAMPLE 1

This example illustrates the applicant's two-step process for converting ginkgolide C to ginkgolide B.

Step 1

To a solution of pyridine (6 ml) in dichloromethane (150 ml) cooled back to −15° C. was added 11.4 ml of trifluoromethane sulfonic anhydride at a temperature lower than −10° C. A solution of ginkgolide C (26.4 g) in pyridine (225 ml) was added at the same temperature. The mixture was stirred for 2 hours at −15° C. and then the temperature was allowed to rise to room temperature. The mixture was concentrated under reduced pressure and the residue was treated with ethyl acetate (150 ml). The solution obtained was washed with hydrochloric acid 1N (75 ml), then twice with a solution of sodium chloride (75 ml). The organic phase was treated with activated carbon (3%), dried over magnesium sulfate and concentrated under vacuum. The resultant residue was treated with a mixture of methyl—tertiobutyl ether and heptane (250/300 ml). The suspension was filtered and the solid was washed twice with heptane (50 ml). There was obtained the C-7 trifluoromethane sulfonate of ginkgolide C and the yield was 91%.

Step 2

A solution of tetrabutylammonium borohydride (11.47 mg) in THF (50 ml) was added dropwise to the solution of C-7 trichloromethane sulfonate of ginkgolide C (25.5 g) in 200 ml of THF, at 20° C. The reaction mixture was stirred for 1 hour at 20° C., then cooled to 10° C. and treated with methanol (25 ml). The solution was concentrated and the residue was treated with ethyl acetate (150 ml). The mixture thus obtained was washed with ammonium hydroxide (60 ml), a solution at 20% by weight of sodium chloride (60 ml), hydrochloric acid 1N (60 ml) and then a solution of sodium chloride (15 ml). The solvent was eliminated under reduced pressure and the obtained residue was treated with a water/ethanol mixture (300/100 ml). The resultant solution was cooled and the product recrystallized. The product was filtered off, washed and then dried. The resulting product was ginkgolide B and the yield was 85.8%.

EXAMPLE 2

Example 1 was repeated except that methanesulfonic anhydride was used instead of trifluoromethane sulfonic anhydride in step 1. The yield from the first step was 90.5%. The yield from the second step, which was carried out in the same manner as set forth in Example 1, was 84% of ginkgolide B.

EXAMPLE 3

Example 1 was repeated except that n-butane sulfonate was used instead of trifluoromethane sulfonic anhydride in step 1. The yield from the first step was 87%. In the second step, sodium borohydride was substituted for the tetrabutylammonium borohydride. The yield of ginkgolide B was 80.2%.

EXAMPLE 4

Example 2 was repeated except that benzene sulfonic anhydride was substituted for the trifluoromethane sulfonic anhydride in the first step. The yield was 86%. After the second step, which was carried out in the same manner as set forth in Example 1, the yield of ginkgolide B was 83%.

EXAMPLE 5

Example 1 was repeated except that toluene sulfonic anhydride was used in place of trifluoromethane sulfonic anhydride in the first step. The yield after the first step was 90%. The second step, carried out as in Example 1, resulted in an 86.7% yield of ginkgolide B.

EXAMPLE 6

Example 1 was repeated except that t-2,4,6-trinitrobenzene sulfonic anhydride was used instead of trifluoromethane sulfonic anhydride in step 1. The yield from the first step was 86%. The second step was carried out in the same manner as Example 1 and the yield was 83% of ginkgolide B.

It will be understood that the claims are intended to cover all changes and modifications of the preferred embodiments of the invention herein chosen for the purpose of illustration which do not constitute a departure from the spirit and scope of the invention.

What is claimed is:

1. Process for the preparation of ginkgolide B from ginkgolide C, said process comprising the following two steps:
   (a) reacting ginkgolide C with a sulfonic anhydride to obtain a C-7 sulfonate of ginkgolide C; and
   (b) reacting the C-7 sulfonate of ginkgolide C with a borohydride in an aprotic solvent, the reaction eliminating the C-7 radical of the C-7 sulfonate of ginkgolide C, thus producing ginkgolide B.

2. The process of claim 1 wherein the reaction of step (a) is effected in a basic medium at a temperature of from about −20° C. to about 35° C. and for a period of from about 15 minutes to about 3 hours.

3. The process of claim 1 wherein the reaction of step (b) is effected at a temperature of from about 10° C. to about 30° C. and for a period of from about 15 minutes to about 3 hours.

4. The process of claim 1 wherein the sulfonic anhydride is an $R_1$-sulfonic anhydride of the formula $(R_1SO_2)_2O$ and wherein $R_1$ is selected from the group consisting of a halogen, a lower alkyl ($C_1$–$C_6$), a halogen substituted lower alkyl, a phenyl, and a halo- or nitro-substituted phenyl.

5. The process of claim 4 wherein R is selected from the group consisting of methyl, n-butyl, trifluoromethyl, toluene, p-nitrophenyl, p-bromophenyl and 2,4,6-trinitrophenyl.

6. The process of claim 1 wherein the borohydride is an $R_2$-borohydride and wherein $R_2$ is selected from the group consisting of alkali metals and alkyl, aryl, or alkyl-aryl substituted ammoniums.

7. The process of claim 6 wherein the alkali metal is sodium.

8. The process of claim 6 wherein R is selected from the group consisting of tetraarylalkylammonium and tetraalkylammonium.

9. The process of claim 1 wherein the borohydride is tetrabutylammonium borohydride.

10. The process of claim 1 wherein the reaction of step (a) is carried out in a solvent selected from the group consisting of pyridine, a mixture of pyridine and dichloromethane, a mixture of acetonitrile and triethylamine, 4-dimethylaminopyridine (DMAP) and imidazole.

11. The process of claim 10 wherein the reaction of step (a) is carried out in pyridine.

12. The process of claim 1 wherein the reaction of step (b) is carried out in tetrahydrofuran.

* * * * *

UNITED STATES PATENT AND TRADEMARK OFFICE
CERTIFICATE OF CORRECTION

PATENT NO. : 5,599,950
DATED : February 4, 1997
INVENTOR(S) : Beng-Poon Teng

It is certified that error appears in the above-indentified patent and that said Letters Patent is hereby corrected as shown below:

Column 2, line 38, change "R" to --$R_1$--; line 42, change "metal" to --alkali metals--; line 47, after "wherein" insert --the--.

Column 4, line 36 (claim 5), change "R" to --$R_1$--.

Column 4, line 45 (claim 8), change "R" to --$R_2$--.

Signed and Sealed this

First Day of April, 1997

Attest:

BRUCE LEHMAN

*Attesting Officer*     *Commissioner of Patents and Trademarks*